US009392987B2

(12) United States Patent
Popova et al.

(10) Patent No.: US 9,392,987 B2
(45) Date of Patent: Jul. 19, 2016

(54) METHOD FOR ASSISTED POSITIONING OF AN ORGAN ON A PLATFORM OF A MEDICAL IMAGING SYSTEM

(71) Applicant: GENERAL ELECTRIC COMPANY, Schenectady, NY (US)

(72) Inventors: Yana Popova, Courbevoie (FR); Henri Souchay, Versailles (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/689,661

(22) Filed: Apr. 17, 2015

(65) Prior Publication Data

US 2015/0327822 A1    Nov. 19, 2015

Related U.S. Application Data

(63) Continuation of application No. 13/334,448, filed on Dec. 22, 2011, now Pat. No. 9,020,094.

(30) Foreign Application Priority Data

Jan. 3, 2011    (FR) ..................................... 11 50020

(51) Int. Cl.
*G03B 42/02*    (2006.01)
*A61B 6/08*    (2006.01)
(Continued)

(52) U.S. Cl.
CPC ................. *A61B 6/502* (2013.01); *A61B 6/025* (2013.01); *A61B 6/04* (2013.01); *A61B 6/0414* (2013.01); *A61B 6/08* (2013.01); *A61B 6/547* (2013.01)

(58) Field of Classification Search
USPC ............. 378/4, 14, 20, 21, 23, 27, 37, 39, 62, 378/126, 163, 175, 177, 178, 181, 195–197, 378/205, 206, 208, 210; 250/370.08, 250/370.09
See application file for complete search history.

(56) References Cited

U.S. PATENT DOCUMENTS

| 4,727,565 A | 2/1988 | Ericson |
| 6,196,715 B1 | 3/2001 | Nambu et al. |

(Continued)

FOREIGN PATENT DOCUMENTS

| FR | 2872659 A1 | 1/2006 |
| JP | 2008167928 A | 7/2008 |

(Continued)

OTHER PUBLICATIONS

Unofficial English Translation of French Search Report and Written Opinion issued in connection with FR Application No. 1150020 on Sep. 13, 2011.

(Continued)

*Primary Examiner* — Bernard Souw
(74) *Attorney, Agent, or Firm* — GE Global Patent Operation; Marc A. Vivenzio

(57) ABSTRACT

A method for assisted positioning of an organ is provided. An acquisition system comprises a platform underneath which a detector is placed for the acquisition of radiographic medical images, during which a radiation source is moved over different successive positions with respect to the detector, wherein at least one medical image is acquired at each position of the radiation source. The method comprises illuminating the platform with a light source of the acquisition system to assist the positioning of the organ on the platform; and determining, with a drive unit of the acquisition system, a positioning limit on the platform based on the distance separating the platform and a compression paddle used to compress the organ and based on the position of the light source relative to the detector, wherein the positioning limit on the platform is a limit beyond which the organ must not lie.

20 Claims, 7 Drawing Sheets

(51) Int. Cl.
*A61B 6/04* (2006.01)
*A61B 6/00* (2006.01)
*A61B 6/02* (2006.01)

(56) References Cited

U.S. PATENT DOCUMENTS

| | | | |
|---|---|---|---|
| 8,331,536 B2 * | 12/2012 | Shaw | A61B 6/06 378/154 |
| 8,774,355 B2 | 7/2014 | Claus et al. | |
| 9,020,094 B2 * | 4/2015 | Popova | A61B 6/025 378/126 |
| 2003/0095624 A1 | 5/2003 | Eberhard et al. | |
| 2007/0025525 A1 | 2/2007 | Gilath | |
| 2008/0101537 A1 | 5/2008 | Sendai | |
| 2009/0225936 A1 | 9/2009 | Kashiwagi et al. | |
| 2009/0232271 A1 | 9/2009 | Sendai | |
| 2009/0232273 A1 | 9/2009 | Sendai | |
| 2009/0268865 A1 | 10/2009 | Ren et al. | |
| 2010/0054402 A1 | 3/2010 | Fischer et al. | |
| 2010/0249647 A1 | 9/2010 | Nakayama | |
| 2011/0150178 A1 | 6/2011 | Bernard et al. | |
| 2012/0328074 A1 * | 12/2012 | Souchay | A61B 6/025 378/37 |
| 2014/0119498 A1 | 5/2014 | Bernard et al. | |

FOREIGN PATENT DOCUMENTS

| | | |
|---|---|---|
| JP | 2009291472 A | 12/2009 |
| JP | 2010233875 A | 10/2010 |

OTHER PUBLICATIONS

Unofficial Translation of Chinese Office Action and Search Report from CN Application No. 201210012998.8 on Oct. 24, 2014.

* cited by examiner

METHOD FOR ASSISTED POSITIONING OF AN ORGAN ON A PLATFORM OF A MEDICAL IMAGING SYSTEM

CROSS-REFERENCE TO RELATED APPLICATIONS

This application is a continuation of U.S. patent application Ser. No. 13/334,448, filed on Dec. 22, 2011, which claims foreign priority benefits to French Application No. 1150020, filed on Jan. 3, 2011, all of which are incorporated by reference herein in their entireties.

BACKGROUND OF THE INVENTION

1. Field of the Invention

This application is a continuation of U.S. patent application Ser. No. 13/334,448, filed on Dec. 22, 2011, which claims foreign priority benefits to French Application No. 1150020, filed on Jan. 3, 2011, all of which are incorporated by reference herein in their entireties.

Embodiments of the present invention relate to the field of radiography using tomosynthesis, and more particularly the field of methods for assisted positioning of an organ, e.g. a breast, for a radiography session by tomosynthesis.

2. Description of the Prior Art

Mammography is conventionally two-dimensional radiography. The patient's breast is positioned on a breast platform with respect to a harmless radiation light source, and then compressed by a compression paddle. The breast is positioned so that it is entirely irradiated by the rays of the X-ray source, i.e. an imaged field illuminated by the light source is the same as the field illuminated by the X-ray source.

For this purpose, when positioning the breast, the imaged field and the breast are illuminated by a light source. Since the light source and the X-ray source cannot physically occupy the same position, a mirror is provided to deflect the light source so that it virtually merges with the X-ray source and illuminates the same imaged field as the X-ray source. It is therefore easy to know which part of the breast will be illuminated by the X-ray source.

Another type of mammary radiography also exists, allowing a three-dimensional image of this organ to be obtained: mammary radiography by tomosynthesis.

With mammary radiography by tomosynthesis, several images of a breast, which is held in position, are acquired at different positions of an X-ray source of an acquisition system with respect to a detector. Usually, the breast is positioned on a breast platform in which the detector of the acquisition system is arranged. The breast is then compressed by a compression paddle. Several images are then acquired with the source moving from a starting position to a finishing position; the breast, the platform and the paddle remain in position. The source describes a movement with respect to the detector. This movement is generally a rotation about a point located on a plane passing through the breast, in the center of the edge of the detector lying opposite the patient.

A 3D image of the breast is then reconstructed from the acquired images. The quality of reconstruction depends upon the beam angle (angle between the two end positions of the source) and the number of acquired images.

Contrary to conventional 2D mammography, with breast radiography by tomosynthesis, several images of the breast are taken at different positions of the X-ray source. It is therefore not possible to know which parts of the breast will be irradiated by the X-ray source at all the positions thereof.

At each of its positions, the X-ray source effectively illuminates a different portion of the space between the source and the detector.

Therefore, if the positions of the breast are simply controlled in the same way as for conventional 2D mammography, it will only be possible to position the breast correctly for one single position of the X-ray source.

In addition, the possible illumination of the entire breast also depends on the breast thickness.

FIGS. 1 and 2 illustrate the positioning of breasts O1 and O2 having a different thickness when they are compressed by the compression paddle 26, and the portion of space illuminated by the source 24 at each of the successive positions S1-S9 thereof (here, as an example, nine positions are illustrated but there may be a different number of positions).

For reasons related to health safety, the illumination cone produced by the source 21 must not project too far beyond the detector 251 to avoid unnecessary patient irradiation.

FIG. 1 shows a compressed breast O1 of small thickness, typically of 3 cm. It is noted that, irrespective of the position of the source 21, this compressed breast O1 is entirely illuminated. Therefore, each of the acquired images contains information on the entirety of the breast O1. The reconstructed 3D image will thus have a good quality and will be reliable.

FIG. 2 illustrates a compressed breast O2 of large thickness, e.g. 12 cm, whose width is identical to that of the compressed breast O1 of small thickness in FIG. 3. During the acquisition of images, at some source positions (solid line—S1-S3 and S7-S9), parts PO2 of the breast O2 are projected outside the detector 251. At these positions, the image acquired by the detector 251 does not contain any information on these non-irradiated parts PO2. During three-dimensional reconstruction (3D) of the breast O2, the lack of information in these images creates artefacts. The volume reconstruction of the breast does not give a true representation thereof.

This problem particularly occurs during radiography in cranio-caudal mode (CC—the detector lies parallel to the floor) with respect to the two side lobes of the breast, and in mediolateral-oblique mode (MLO—the detector lies 45° to the vertical) with respect to the lower breast lobe.

At the present time, no method is available to remedy the lack of information on a part of the breast in the acquired images.

BRIEF SUMMARY OF THE INVENTION

According to one embodiment of the present invention, a method for assisted positioning of an organ on a platform is provided. An acquisition system comprises the platform underneath which a detector is placed for the acquisition of radiographic medical images by tomosynthesis, during which a radiation source for irradiating the organ is moved over different successive positions with respect to the detector, from a starting position to a finishing position, wherein at least one medical image is acquired at each position of the radiation source. The method comprises illuminating the platform with a light source of the acquisition system to assist the positioning of the organ on the platform; and determining, with a drive unit of the acquisition system, a positioning limit on the platform based on the distance separating the platform and a compression paddle used to compress the organ and based on the position of the light source relative to the detector, wherein the positioning limit on the platform is a limit beyond which the organ must not lie.

The operator in charge of positioning the patient, and hence the organ to be imaged, is provided with a visual aid that is easily interpreted for determining which portion of space above the detector will be illuminated by the X-ray source at all positions thereof.

In addition, this method does not require major modifications to the acquisition system. It is therefore easy to implement.

According to another embodiment of the present invention, a medical imaging system is provided. The medical imaging system comprises an acquisition unit comprising a light source, a detector, a platform underneath which the detector is placed for acquisition of radiographic medical images by tomosynthesis, a compression paddle used to compress an organ, and a positioner configured to position the source at acquisition positions with respect to the detector. The medical imaging system also comprises a drive unit configured to determine a positioning limit on the platform, based on the distance separating the platform and the compression paddle and based on the position of the light source with respect to the detector, wherein the positioning limit on the platform is a limit beyond which the organ must not lie, and wherein the detector is illuminated with the light source to mark out the positioning limit.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION OF THE INVENTION

Figure 1:
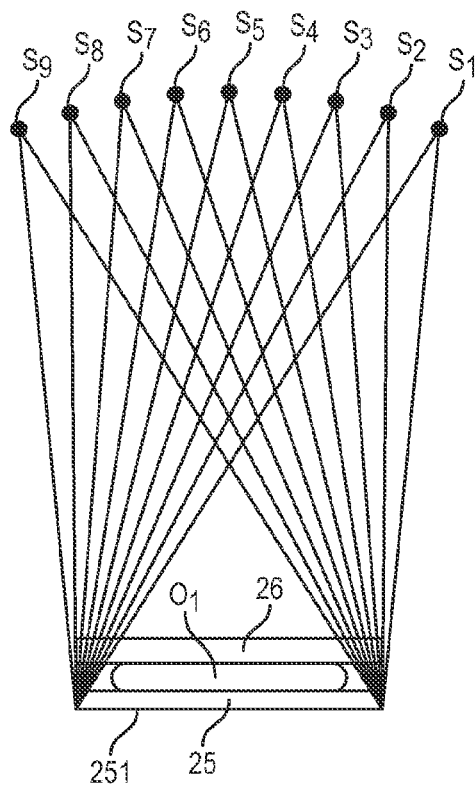
FIG. 1 illustrates the 3D illumination of a breast of small thickness at each of the positions of a source of an acquisition system in accordance with an embodiment of the present invention.
Figure 2:
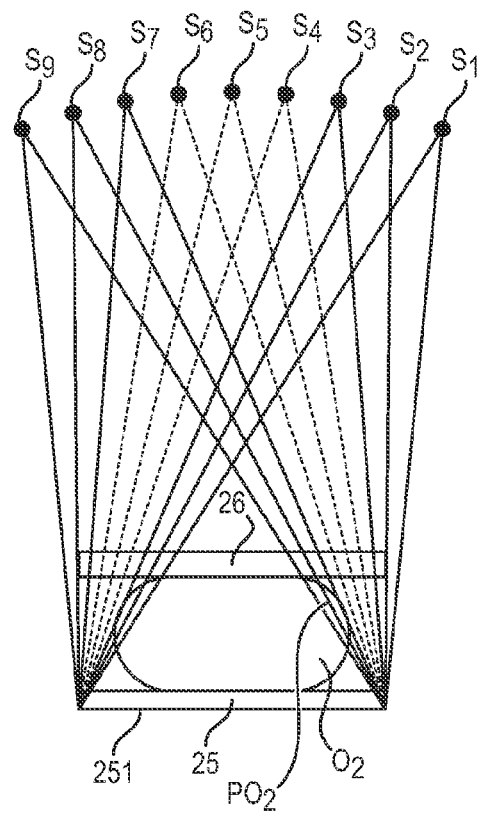
FIG. 2 illustrates the 3D illumination of a breast of large thickness at each of the positions of a source of an acquisition system in accordance with an embodiment of the present invention.
Figure 3:
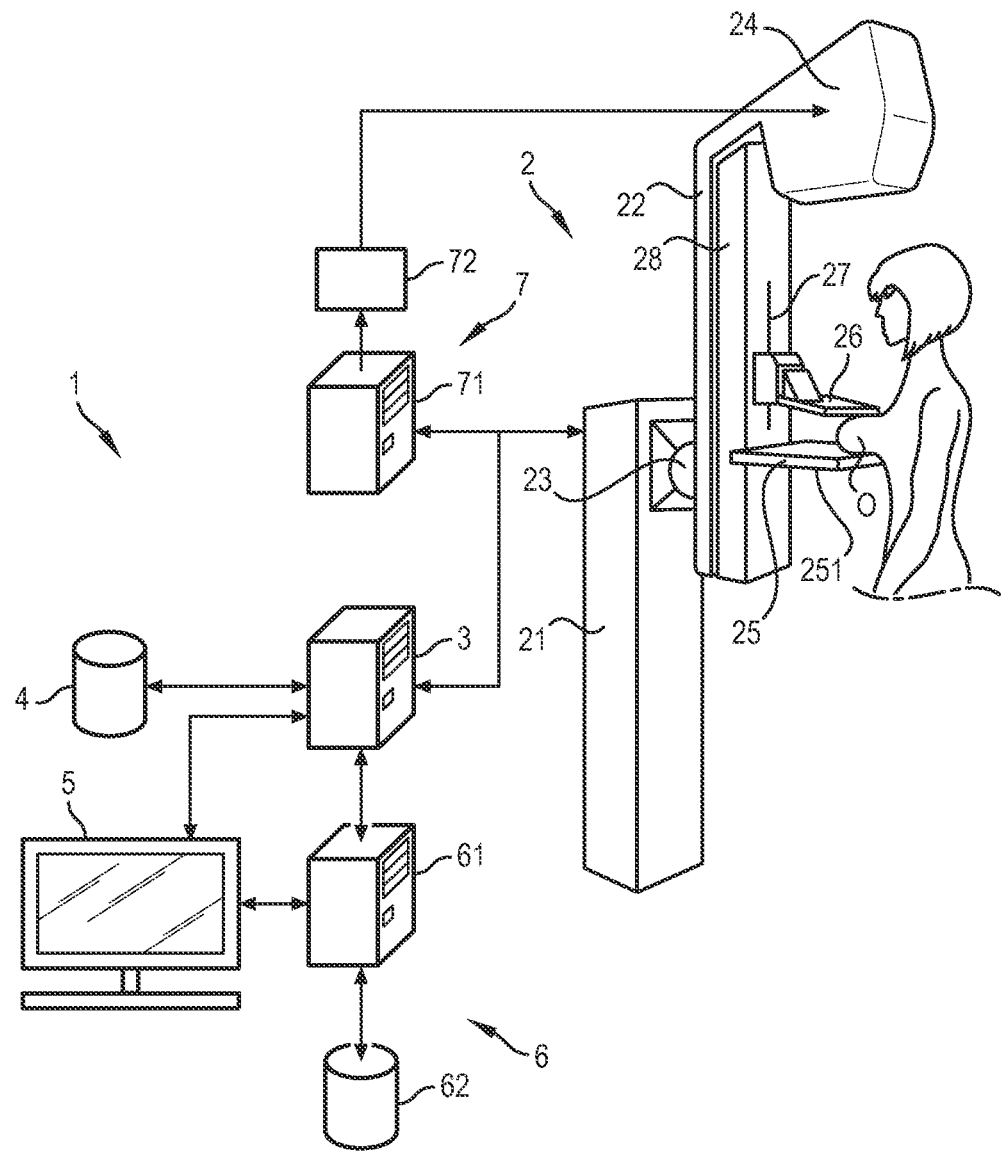
FIG. 3 illustrates an acquisition system according to an embodiment of the invention.
Figure 4:
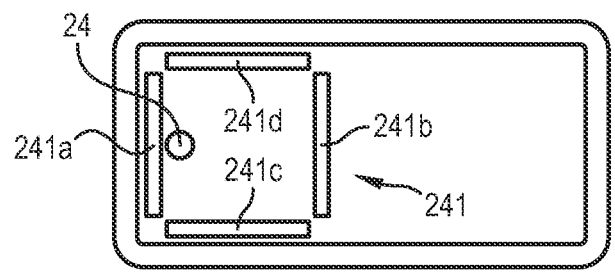
FIG. 4 illustrates a collimator used in the acquisition system in FIG. 3, as seen from an underside view.

FIGS. 3 and 4 schematically illustrate a medical imaging system 1 for the acquisition of images allowing three-dimensional (3D) reconstruction of a breast O from two-dimensional images (2D) of the breast O. The medical imaging system 1 is shown coupled with a module for generating images evidencing suspect regions of the breast O.

The medical imaging system 1 may be mammography equipment for the detection and characterization of radiological signs for the screening, diagnosis and treatment of breast cancer (tissue matrix).

The medical imaging system 1 comprises a 2D image acquisition unit 2. The acquisition unit 2 chiefly comprises a detector 251 lying opposite a radiation source and illuminated by the latter during the acquisition of medical images. The radiation source is mobile relative to the detector 251. Optionally, the detector 251 may also be mobile relative to the radiation source.

A more thorough example of an acquisition system 1 is given below.

The acquisition unit 2 for example comprises a vertical support 21 and a positioning arm 22 linked to a radiation source, e.g. X-ray source, and optionally a harmless light source dedicated to illumination when positioning the breast O to be imaged. The positioning arm 22 is rotatably joined to the vertical support 21 about a rotation shaft 23. The vertical support 21 is fixed. Therefore, by rotating the positioning arm 22, the radiation source can be positioned in determined orientations.

The acquisition unit 2 also comprises a supporting arm 28 provided with a stage comprising a breast platform 25 and a compression paddle 26 parallel to the breast platform 25 for compressing the breast O positioned on the breast platform 25, as illustrated in FIG. 3. The compression paddle 26 is positioned above the breast platform 25 and can be moved in translation relative to the latter along a translation rail 27. The breast platform 25 comprises a radiation detector 251 to detect radiation used by the radiation source. The breast platform 25 and compression paddle 26 hold the breast O immobile during the acquisition of medical images.

The breast platform 25 and the compression paddle 26 may be planar. They may or may not be positioned parallel to the floor, for example at 45°. The supporting arm 28 may be rotatably mounted on the vertical support 21, advantageously with the same axis of rotation as the positioning arm 22.

In this latter case, the positioning arm 22 and supporting arm 28 are separate, enabling the rotation of one relative to the other about a rotation shaft 23. They are positioned relative to one another so that a large part of the radiation emitted by the radiation source is received by the detector 251.

The detector 251 may be a semiconductor image sensor, for example comprising caesium iodide phosphorus (scintillator) on a transistor/photodiode array in amorphous silicon. Other suitable detectors are: CCD sensor, direct digital detector directly converting X-rays into electronic signals. The detector 251 illustrated in FIG. 3 is planar and defines a planar image surface, other geometries possibly being suitable e.g. digital X-ray detector of curved shape forming a curved image surface, or detectors which move during acquisition.

The acquisition unit 2 also comprises a collimator 241 placed underneath the radiation source to delimit the portion of space illuminated by the radiation source (see FIG. 4 in which reference 24 denotes both the radiation source and a light source). The collimator 241 comprises four plates 241a-241d which can be independently moved relative to one another. A first plate 241a is placed between the center of rotation of the source and the patient's chest (front plate). The first plate 241a blocks out part of the radiation from the radiation source that is directed towards the patient. A second plate 241b (rear plate) is placed opposite the first plate 241a. The second plate 241b blocks out part of the radiation from the radiation source that is directed towards the front of the detector 251. Finally, two side plates 241c and 241b block part of the radiation from the radiation source directed laterally.

The medical imaging system 1 further comprises a drive unit 7 to drive the plates of the collimator 241. This drive unit 7 is linked to the acquisition unit 2 and receives data from the latter on the distance between the compression paddle 26 and the detector 251, and on the position of the radiation source for example. The drive unit 7 comprises a computer 71 computing movement of the plates 241a-241d, and an actuator 72 to actuate the plates 241a-241d.

The medical imaging system 1 also comprises a control unit 3 connected to the acquisition unit 2 via a wire link or via a network. The control unit 3 sends electric control signals to the acquisition unit 2 to set several parameters such as the radiation dose to be emitted, the angular position of the positioning arm 22, the angular position of the supporting arm 28, the compression force to be applied by the compression paddle 26 to the breast O.

The control unit 3 may comprise a reader device (not illustrated) e.g. a diskette reader, CD-ROM, DVD-ROM reader, or connection ports to read the instructions of the processing method from an instruction medium (not shown) such as a diskette, CD-ROM, DVD-ROM, USB stick or more generally any removable memory medium, or via a network connection.

As a variant, the control unit 3 may comprise a wire or wireless network connection device (not illustrated). As a variant, the control unit 3 carries out the instructions for the processing method stored in firmware.

The medical imaging system 1 further comprises a memory unit 4 linked to the control unit 3 to record parameters and acquired images. It is possible for the memory unit 4 to be provided inside or outside the control unit 3.

The memory unit 4 can be formed of a hard disk or SSD, or any other removable, re-write storage means (USB sticks, memory cards, etc.).

The memory unit 4 can be a ROM/RAM memory of the control unit 3, USB sticks, memory card, memory of a central server.

The medical imaging system 1 comprises a display unit 5 linked to the control unit 3 to display acquired images and/or data on parameters which the control unit 3 must transmit to the acquisition unit 2.

The display unit 5 can be integrated in the acquisition unit 2 or in the control unit 3 or a 3D computer 61 described below, or it can be separate as is the case for example of a viewing station used by the radiologist to determine diagnosis from digital medical images.

The display unit 5 is for example a computer screen, a monitor, flat screen, plasma screen or any type of commercially known display device.

The display unit 5 enables the practitioner to control the reconstruction and/or display of acquired 2D images.

The medical imaging system 1 is coupled with a computing system 6 comprising a 3D computer 61 which receives acquired images stored in the memory unit 4 of the medical imaging system 1, from which it constructs a 3D image of the breast by digital tomosynthesis. An example of a method for breast digital tomosynthesis is described more in detail in document FR 2 872 659.

The computer 61, for example, may be one or more computers, one or more processors, one or more microcontrollers, one or more microcomputers, one or more programmable logical controllers, one or more application-specific circuits, other programmable circuits, or other devices which include a computer such as a work station.

The computing system 6 also comprises a memory unit 62 to store data generated by the 3D computer 61.

Below the description is given with reference to X-ray mammography taken as a specific example. The tissue matrix is therefore the breast in this case. Other kinds of tissue matrix and/or acquisition techniques can be contemplated. The person skilled in the art will be able to adapt the teaching given below to any type of image acquisition technique allowing the same, and to any type of tissue matrix.

Figure 5:
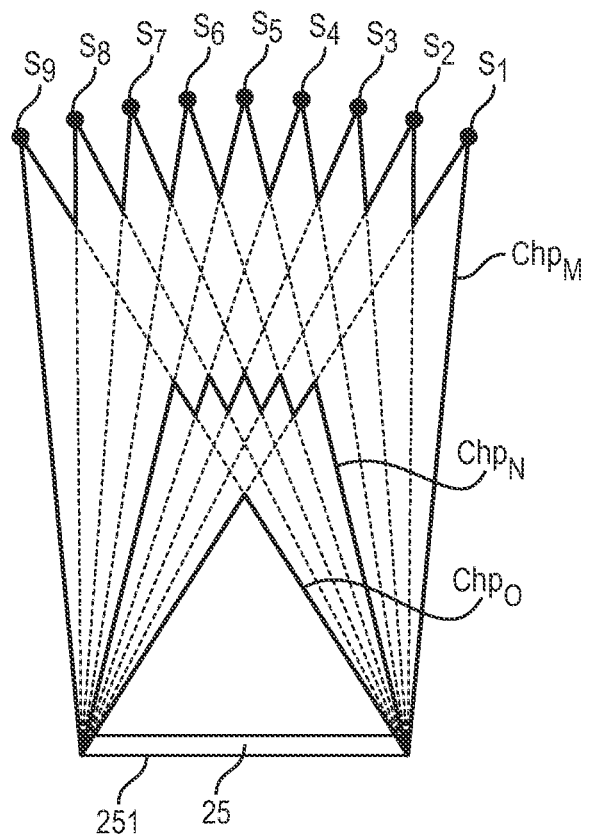
FIG. 5 illustrates definitions of the maximal, nominal and optimal fields.
Figure 6:
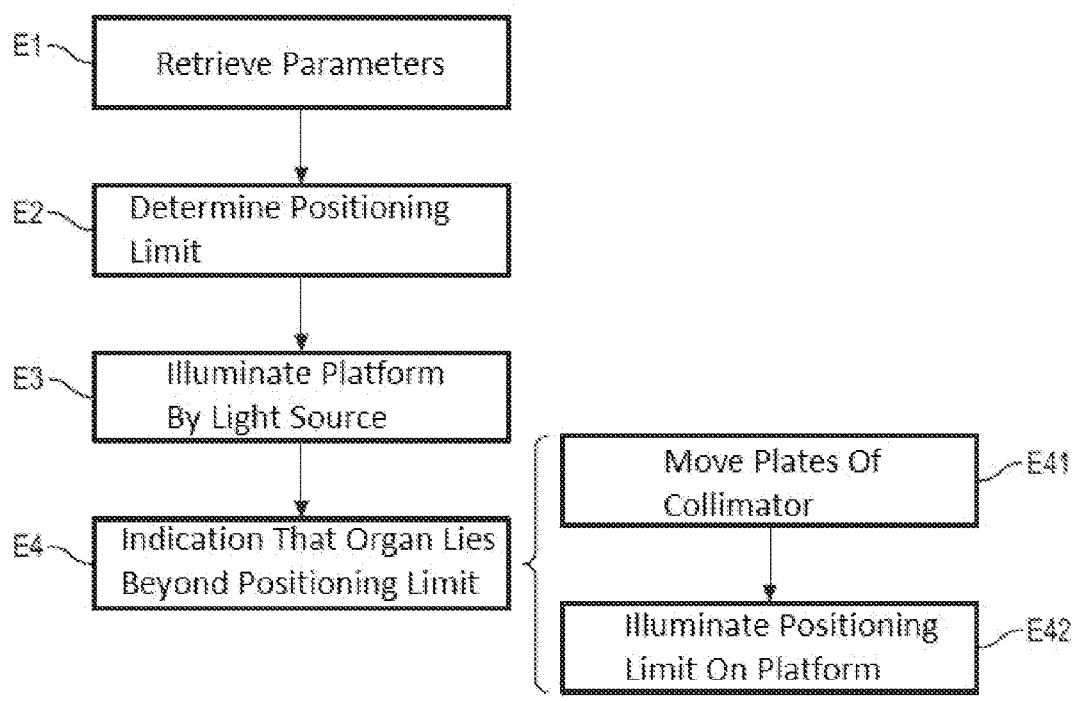
FIG. 6 schematically illustrates the different steps of an assisted positioning method for a breast according to an embodiment of the invention.

For the needs of the following description, three illumination fields of the space above the detector are defined (FIG. 5).

The maximal field $Chp_M$ is the portion of space illuminated by the radiation source at least at one of the image acquisition positions $S_i$, which here total nine for the needs of the description.

The nominal field $Chp_N$ is the portion of space illuminated by the radiation source at least at one half of the positions thereof. For example, in the illustrated example, one half of the positions is 4.5, therefore the nominal field $Chp_N$ is illuminated by the radiation source at least at five positions thereof. In general, if the radiation source is successively positioned at N positions for the acquisition of images, the nominal field $Chp_N$ is the portion of space illuminated by the radiation source at M positions, M being at least equal to:

$$E\left(\frac{N}{2}\right) + 1, \text{ if } N \text{ is uneven;}$$

$$E\left(\frac{N}{2}\right), \text{ if } N \text{ is even;}$$

E being the function which assumes the value of the integer part of the number to which it is applied.

More generally, the nominal field $Chp_N$ can be defined as the portion of space illuminated by the source at least at K positions, K being different from 1 (maximal field $Chp_M$) and from N (optimal field $Chp_O$).

The optimal field $Chp_O$ is the portion of space illuminated by the radiation source at all the image acquisition positions $S_{1-N}$, for example in the illustrated case at the nine positions $S_{1-9}$. The optimal field $Chp_O$ is always delimited by the radiation source at the end positions (starting position $S_D = S_1$ and finishing position $S_A = S_N$).

Below, with reference to FIGS. 6 to 9, a description is given of a method for the assisted positioning of the breast on a breast platform in an medical imaging system, underneath which a detector is placed for the acquisition of radiological medical images using tomosynthesis.

During a session for the acquisition of medical images by tomosynthesis, a radiation source is moved with respect to the detector 251 over different successive positions $S_1$-$S_N$ from a starting position $S_D$ to a finishing position $S_A$ for irradiating the breast O. At each position, the radiation source irradiates the breast O and the detector 251 acquires at least one medical image.

As explained in the foregoing, during a medical image acquisition session using conventional tomosynthesis, the radiation source does not irradiate the breast O in its entirety. Notably, some parts such as the lobes, at some positions of the radiation source, may not be irradiated by the source, causing artefacts when reconstructing the three-dimensional image from the acquired medical images.

This is remedied by the method upstream i.e. even before the medical images are acquired.

The method firstly comprises the retrieval E1 by the drive unit 7 of parameters for the positioning of the parts of the acquisition unit 2 used.

Next, a positioning limit is determined E2 by a computer 71 of the drive unit 7, to indicate to the operator that the breast O is properly positioned i.e. during the subsequent acquisition of medical images and during construction of the three-dimensional image from these medical images, generated artefacts are minimized (i.e. the breast O is positioned so that it lies in the nominal field $Chp_N$), or eliminated (i.e. the breast O is positioned so that it lies in the optimal field $Chp_O$).

This positioning limit marks the area beyond which the breast O must not lie once the breast is positioned, to limit and even eliminate artefacts. The positioning limit depends on positioning parameters of elements of the acquisition unit 2. It is determined on the basis of these parameters previously retrieved by the drive unit 7.

Since the nominal $Chp_N$ and optimal $Chp_O$ fields are portions of space whose size decreases when moving away from the detector 251, the compression of the breast O needed for acquisition of the medical images is a data item of importance. The positioning limit is therefore determined by the drive unit 7, comprising a computer 71 for this purpose, basing determination at least on the distance B separating the breast platform 25 from compression paddle 26 of the acquisition unit 2 used to compress the breast O, and on the position of the light source 24 with respect to the detector 251. For example, distance B is sent by the acquisition unit 2 to the computer 71 of the drive unit 7.

The positioning limit can be determined so that the breast O once compressed by the compression paddle 26 lies fully in the nominal field $Chp_N$, or even better in the optimal field $Chp_O$.

The method comprises the illumination E3 of the breast platform 25 by a light source 24 of the acquisition unit 2. This light source 24 is harmless for the tissues and hence for the patient.

This illumination of the breast platform 25 by the light source 24 assists the operator in positioning the breast O on the breast platform 25 by improving luminosity.

Finally, the method comprises the indication E4 that the breast O lies beyond the positioning limit, this indication possibly being made in several manners. For example, this indication can be a sound or visual indication.

In one embodiment, the drive unit 7 controls the light source 24 to mark the positioning limit by partial illumination of the breast platform 25, thereby providing a visual indication. In this embodiment, the illuminating step E3 and indication step E4 may be merged.

By illuminating the breast platform 25, the light source 24 also illuminates the detector 251 placed underneath the breast platform 25 in an area corresponding to the illuminated area of the breast platform 25.

During this step, an actuator 72 of the drive unit 7 suitably and dynamically moves E41 the plates 241a-241d of a collimator 241 arranged under the light source 24, with respect to the distance between the compression paddle 26 and the breast platform 25 or the detector 251. The illumination step itself is then conducted E42.

Therefore, during positioning of the patient, and hence of the breast O, the operator is able to visualize the parts of the breast which lie in the optimal field $Chp_O$ (or nominal field $Chp_N$ as applicable). The illuminated area of the detector 251 will be visible (via the illuminated part of the breast platform 25). The collimator 241 is driven automatically by the actuator 72 of the drive unit 7 simultaneously with translation of the compression paddle 26 along the translation rail 27.

Below several examples of implementation of the method are described more in detail.

Figure 7:
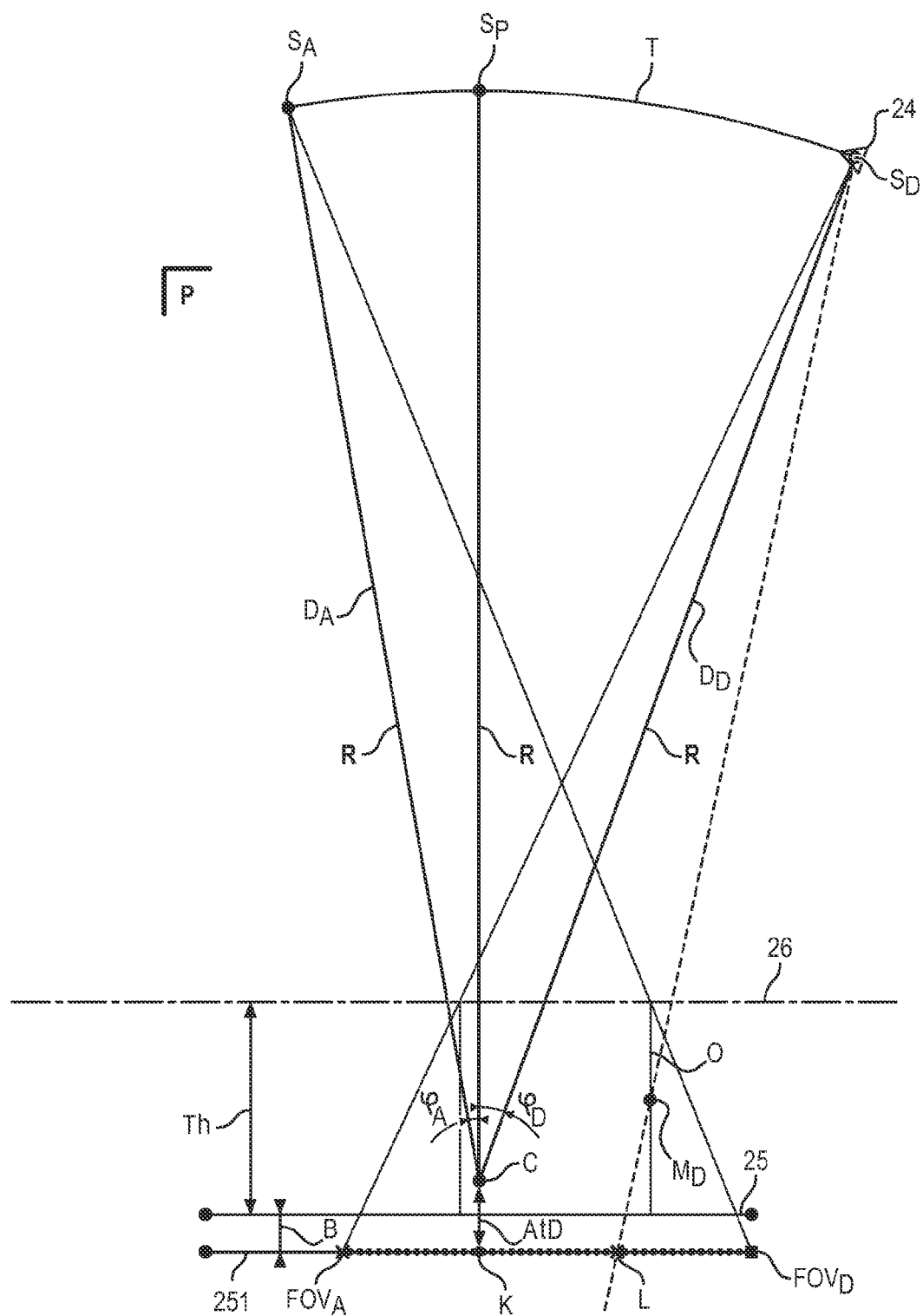
FIG. 7 illustrates a first embodiment of the step of illuminating the detector of the acquisition system through a breast platform, by marking the positioning limit using a light source placed at an end position of the radiation source.

In a first example of implementation illustrated in FIG. 7, the light source 24 is positioned at an end position of the radiation source. This end position may be the starting position $S_D$ or finishing position $S_A$ of the radiation source for illumination of the breast platform 25 from this position $S_D$ or $S_A$. For example, if nine positions of the radiation source are used for acquiring the medical images, and numbered in the order of positioning of the radiation source, the first position is the starting position $S_D$ and the ninth position $S_9$ is the finishing position $S_A$.

In one particular embodiment of the acquisition of medical images by tomosynthesis, the radiation source defines a circular trajectory T about a center C, of radius R, when it is moved from one position to the next.

In this case, the parameters which are used below are defined in a sectional plane P passing through (including) the center C of the circular trajectory T, the starting position $S_D$ and the finishing position $S_A$.

A first illumination cone (or cone on the starting side) $C_D$ of the radiation source, in the sectional plane P, defines a first point (or point on the finishing side) $FOV_A$ on the detector 251. This point on the finishing side $FOV_A$ is the radiation limit of the illumination source on the side of the finishing position $S_A$ when the radiation source is placed in the starting position $S_D$.

A second illumination cone (or cone on the finishing side) $C_A$ of the radiation source, in this sectional plane P, defines a second point (or point on the starting side) $FOV_D$ on the detector 251. This point on the starting side $FOV_D$ is the radiation limit of the illumination source on the side of the starting position $S_D$ when the radiation source is placed at the finishing position $S_A$.

The straight line connecting the point on the starting side $FOV_D$ with the finishing position, and the straight line connecting the point on the finishing side $FOV_A$ with the starting position $S_D$ define the limits of the optimal field $Chp_O$.

The starting position $S_D$ and the finishing position $S_A$ can be asymmetric relative to a plane including the center C of the circular trajectory T and the sectional plane P. This situation is notably used for mammary radiography by tomosynthesis in MLO mode. In MLO mode, the surface of the detector 251 is tilted relative to the floor at an angle of ±45°. So as to avoid patient discomfort and especially to avoid impacting the patient, the successive positions (generally spatial incrementing is constant) of the radiation source are distributed on the free side i.e. if the left—respectively right—breast is imaged, there will be more positions on the right—respectively left—side of the patient.

The starting position $S_D$ and the finishing position $S_A$ may be symmetrical relative to the plane comprising the center C of the circular trajectory T and the sectional plane P. This situation is advantageous for mammary radiography by tomosynthesis in CC mode. In CC mode, the surface of the detector 251 lies parallel to the floor. The distribution amplitude of the successive positions (generally spatial incrementing is constant) of the radiation source may be symmetrical and the positions equally distributed between the right side and left side of the patient.

If the light source 24 is in the starting position $S_D$ when it illuminates the detector 251 (through the breast platform 25), it illuminates the detector 251 at least in an area lying between the point on the finishing side $FOV_A$ and a limit point L defined on the sectional plane P and on the detector 251 by the following formula:

$$L = R\sin(-\varphi_D) - \frac{\left[R\sin(-\varphi_D) - \left(FOV_D - (Th + B)\left(\frac{R\sin(\varphi_A) + FOV_D}{R\cos(\varphi_A) + AtD}\right)\right)\right]}{R\cos(\varphi_D) + AtD - \left(B + \frac{Th}{2}\right)}.$$

AtD is the orthogonal distance on the sectional plane P between the center C of the circular trajectory T and the detector 251. Th is the orthogonal distance on the sectional plane P between the surface of the breast platform 25 on which the breast O is positioned and the compression paddle 26. The parameter φD, respectively φA, is the trigonometric angle on the sectional plane P defined between a straight line perpendicular Dp to the detector 251 passing through the center C of the circular trajectory T and a straight line $D_D$, respectively $D_A$, joining the center C of the circular trajectory T with the starting position $S_D$, respectively finishing position $S_A$; B is the orthogonal distance on the sectional plane P between the surface of the breast platform 25 on which the breast O is positioned and the detector 251.

The origin for measuring points $FOV_D$, $FOV_A$ and L is the orthogonal projection K on the detector 251 of center C of the circular trajectory T.

This limit point L is computed firstly by determining the parallelepiped of height equal to distance Th placed over the surface of the breast platform 25 and schematically representing the breast O. The parallelepiped on the sectional plane P defines a rectangle. From this rectangle, a mid-point on the starting side $M_D$ is determined. This mid-point on the starting side $M_D$, on the sectional plane P, is the middle of one side of the rectangle non-parallel to the detector 251 and located closest to the starting position $S_D$. By then causing a straight line to pass through this mid-point on the starting side $M_D$ and the starting position $S_D$, the limit point L is determined as the intersection on the sectional plane P of the straight line passing through the mid-point on the starting side $M_D$ and the starting position $S_D$ and the detector 251.

If the light source 24 is at the finishing position $S_A$ when it illuminates the detector 251 (through the breast platform 25), it illuminates the detector 251 at least in an area lying between the point on the starting side $FOV_D$ and a limit point L defined on the sectional plane P and on the detector 251 by the following formula:

$$L = R\sin(-\varphi_A) - \frac{\left[R\sin(-\varphi_A) - \left(FOV_A - (Th + B)\left(\frac{R\sin(\varphi_D) + FOV_A}{R\cos(\varphi_D) + AtD}\right)\right)\right]}{R\cos(\varphi_A) + AtD - \left(B + \frac{Th}{2}\right)};$$

with the same parameters as in the preceding part.

This limit point L is in fact computed by determining firstly the parallelepiped, whose height is equal to distance Th, placed over the surface of the breast platform 25 and schematically representing the breast O. The parallelepiped, on the sectional plane P, defines a rectangle. From this rectangle, a mid-point on the finishing side $M_A$ is determined. This mid-point on the finishing side $M_A$, on the sectional plane P, is the middle of one side of the rectangle non-parallel to the detector 251 and located the closest to the finishing position $S_A$. By then causing a straight line to pass through this mid-point on the finishing side $M_A$ and the finishing position $S_A$, the limit point L is determined as the intersection on the sectional plane P of the straight line passing through the mid-point on the finishing side $M_A$ and the finishing position $S_A$ and the detector 251.

Figure 8:
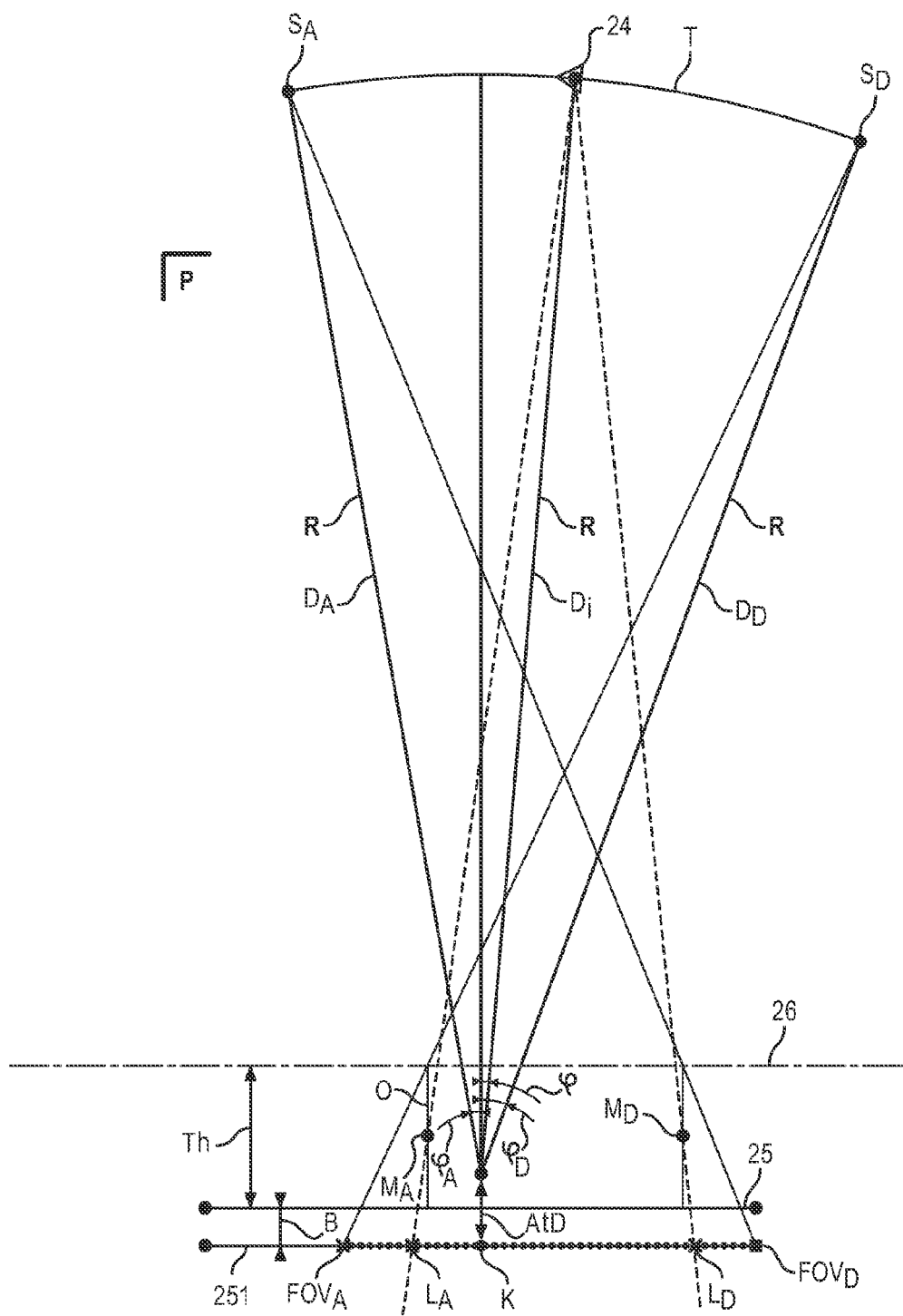
FIG. 8 illustrates a second embodiment of the step of illuminating the detector of the acquisition system through a breast platform, by marking the positioning limit using a light source placed at a position of the radiation source located between the two end positions.

In a second example of implementation, illustrated in FIG. 8, the light source 24 is positioned between the starting position $S_D$ and the finishing position $S_A$ of the radiation source during illumination of the detector 251 to mark the positioning limit. For example, if nine positions of the radiation source are used for the acquisition of medical images and numbered in order of the positioning of the radiation source, the positions on which the light source 24 can be positioned are the positions $S_2$ to $S_{N-1}$, for example the light source 24 occupies the central position between the starting position $S_D$ and the finishing position $S_A$ (if N is even, one of the two most central positions is chosen).

The starting position $S_D$ and the finishing position $S_A$ may be asymmetrical relative to a plane comprising the center C of the circular trajectory T and the sectional plane P. This situation is notably used for breast radiography by tomosynthesis in MLO mode. In MLO mode, the surface of the detector 251 is tilted relative to the floor at an angle of ±45°. So as to avoid patient discomfort and especially to avoid impacting the patient, the successive positions (generally spatial incrementing is constant) of the radiation source are distributed on the free side i.e. if the left—respectively right—breast is imaged, there will be more positions on the right—respectively left—side of the patient.

The starting position $S_D$ and the finishing position $S_A$ may be symmetrical relative to the plane comprising the center C of the circular trajectory T and the sectional plane P. This situation is advantageous for breast radiography by tomosynthesis in CC mode. In CC mode, the surface of the detector 251 lies parallel to the floor. The distribution amplitude of the successive positions (generally spatial incrementing is constant) of the radiation source may be symmetrical and the positions equally distributed between the right and left side of the patient.

In the particular mode of acquisition of medical image already described, the light source 24 illuminates the detector 251, through the breast platform 25, in an area lying between a first limit point (or limit point on the starting side) $L_D$ and a second limit point (or limit point on the finishing side) $L_A$.

The limit point on the starting side $L_D$ and the limit point on the finishing side $L_A$ are defined on the sectional plane P and on the detector 251, respectively on the side of starting position $S_D$ and the finishing position $S_A$.

The limit point on the starting side $L_D$ is defined by the following formula:

$$L_D = R\sin(-\varphi) - \frac{\left[R\sin(-\varphi) - \left(FOV_D - (Th + B)\left(\frac{R\sin(\varphi_A) + FOV_D}{R\cos(\varphi_A) + AtD}\right)\right)\right]}{R\cos(\varphi) + AtD - \left(B + \frac{Th}{2}\right)}.$$

The limit point on the finishing side $L_A$ is defined by the following formula:

$$L_A = R\sin(-\varphi) - \frac{\left[R\sin(-\varphi) - \left(FOV_A - (Th+B)\left(\frac{R\sin(\varphi_D) + FOV_D}{R\cos(\varphi_D) + AtD}\right)\right)\right](R\cos(\varphi) + AtD)}{R\cos(\varphi) + AtD - \left(B + \frac{Th}{2}\right)}.$$

In the two formulae, the parameters are those described in relation to an embodiment where the radiation source defines a circular trajectory T about a center C, of radius R, when it is moved from one position to the next.

In addition, φ is the trigonometric angle on the sectional plane P defined between the straight line $D_p$ perpendicular to the detector 251 passing through the center C of the circular trajectory T, and a straight line $D_i$ joining the center C of the circular trajectory T with position $S_i$ at which the light source 24 is positioned to illuminate the illumination limit.

The limit point on the starting side $L_D$ is in fact computed by firstly determining the parallelepiped, of height equal to distance Th, placed over the surface of the breast platform 25 and schematically representing the breast O. The parallelepiped on the sectional plane P defines a rectangle. From this rectangle, a mid-point on the starting side $M_D$ is determined. This mid-point on the starting side $M_D$, on the sectional plane P, is the middle of one side of the rectangle non-parallel with the detector 251 and located closest to the starting position $S_D$. By then causing a straight line to pass through this mid-point on the starting side $M_D$ and the starting position $S_D$, the limit point on the starting side $L_D$ is determined as the intersection on the sectional plane P of the straight line passing through the mid-point on the starting side $M_D$ and the starting position $S_D$ and the detector 251.

Similarly, the limit point on the finishing side $L_A$ is computed by firstly determining the parallelepiped, of height is equal to distance Th, placed over the surface of the breast platform 25 and schematically representing the breast O. The parallelepiped on the sectional plane P defines a rectangle. From this rectangle, a mid-point on the finishing side $M_A$ is determined. This mid-point on the finishing side $M_A$, on the sectional plane P, is the middle of one side of the rectangle non-parallel to the detector 251 and located closest to the finishing position $S_A$. By then causing a straight line to pass through this mid-point on the finishing side $M_A$ and the finishing position $S_A$, the limit point on the finishing side $L_A$ is determined as the intersection on the sectional plane P of the straight line passing through the mid-point on the finishing side $M_A$ and the finishing position $S_A$ and the detector 251.

Figure 9:
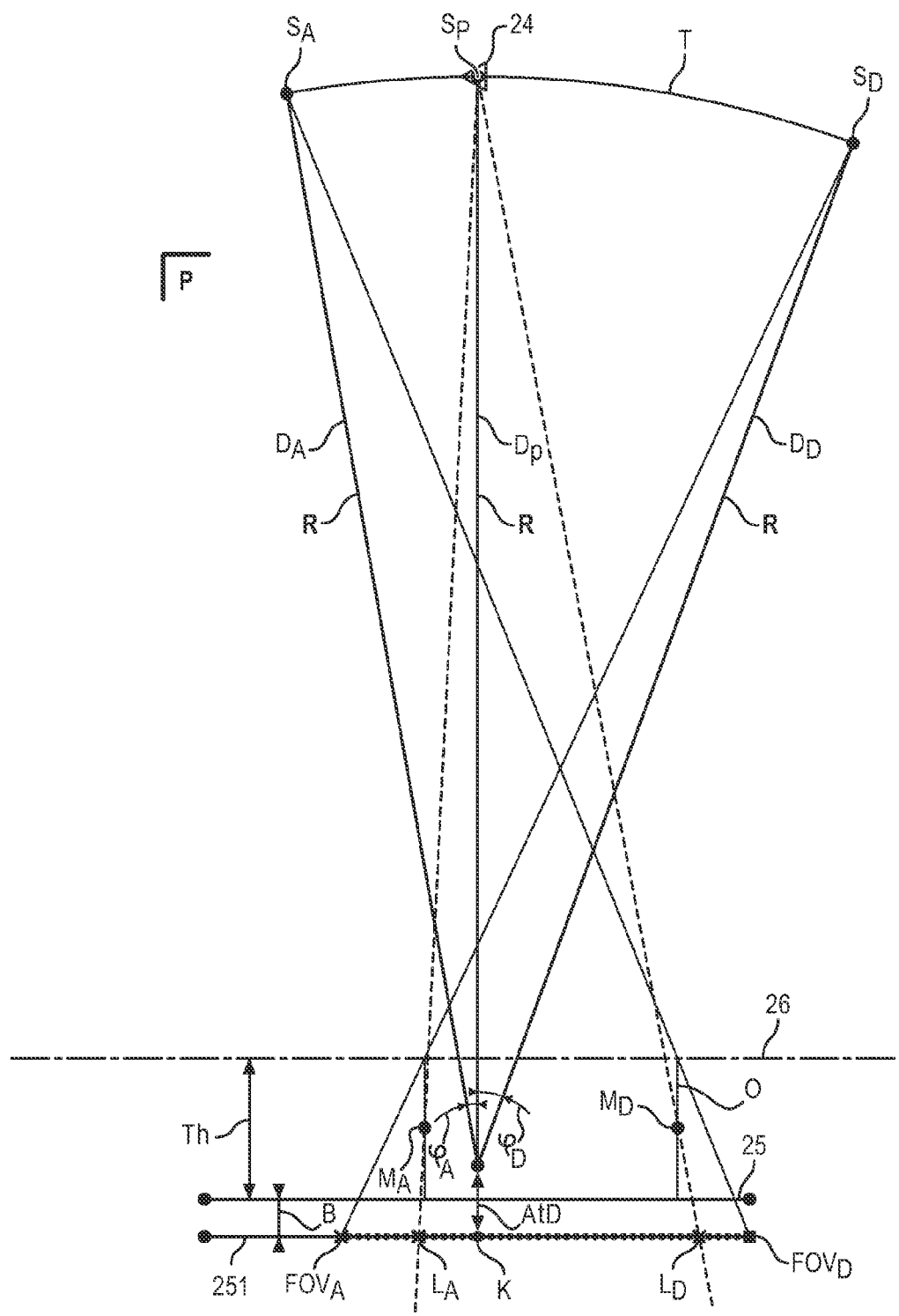
FIG. 9 illustrates a third embodiment of the step of illuminating the detector of the acquisition system through a breast platform, by marking the positioning limit using a light source placed at a position perpendicular to the detector of the radiation source.

In one embodiment illustrated in FIG. 9, the light source 24 is positioned at a position $S_P$ perpendicular to the detector 251, i.e. the straight line $D_i$ at the position of the light source $S_i$ is perpendicular to the detector 251. In this case, the angle φ is zero and the formulae giving the limit points on the starting and finishing sides are simplified:

$$L_D = \frac{\left(FOV_D - (Th+B)\left(\frac{R\sin(\varphi_A) + FOV_D}{R\cos(\varphi_A) + AtD}\right)\right)(R + AtD)}{R + AtD - \left(B + \frac{Th}{2}\right)}; \text{ and}$$

$$L_A = \frac{\left(FOV_A - (Th+B)\left(\frac{R\sin(\varphi_D) + FOV_D}{R\cos(\varphi_D) + AtD}\right)\right)(R + AtD)}{R + AtD - \left(B + \frac{Th}{2}\right)}.$$

In the more particular case in which the starting $S_D$ and finishing $S_A$ positions are symmetrical relative to a straight line, in the sectional plane P, that is perpendicular to the detector 251 and passes through the center of the detector 251, and if $FOV_D = FOV_A$, we have:

LD=LA since φD=φA

The limit points on the starting $FOV_D$ and finishing $FOV_A$ sides may differ from one sectional plane P to another. However, they can easily be determined by the computing unit 7 from manufacturer data on the acquisition unit 2 and notably the collimator 241.

In general, for all the variants described above, the limit points on the starting side $FOV_D$ and finishing side $FOV_A$ may possibly not be symmetrical relative to the center of the detector 251 determined on the sectional plane P. Said off-centring is advantageous for smaller breasts; it provides the operator with better visibility and greater positioning amplitude. In addition, said off-centring is necessary for tomosynthesis radiography in MLO mode. Off-centring allows easier positioning of the breast O, notably smaller breasts, so that it is also possible to image the pectoral muscle above the breast O extending towards the shoulder.

On the contrary, the centring of the limit points on the starting side $FOV_D$ and finishing side $FOV_A$ is advantageous for radiography by tomosynthesis in CC mode.

In addition, the distances B and R are known; these are manufacturer data.

The distance AtD is also known, it is also a manufacturer data. If the distance AtD is not set by the manufacturer, it is either determined by the acquisition unit 2 and retrieved by the computing unit 7, or directly determined by the computing unit 7.

The distance Th is either determined by the acquisition unit 2 and retrieved by the computing unit 7, or determined by the computing unit 7 from the position of the breast platform 25 and the position of the compression paddle 26 determined by the acquisition unit 2. This is also true for the angles φD, φA and φ and more generally for any parameter allowing determination of the position of the light source 24 or radiation source.

The determination of the limit positioning is conducted in real time. In other words, when the distance Th is modified, the positioning limit is again determined to provide the operator with knowledge of the modification of this limit.

In the entirety of the foregoing description of embodiments of the method, the detector 251 is considered as having a planar detection surface. If this detection surface is not planar, the distances are taken with respect to a mean plane of the detector 251.

The method for assisted positioning can be implemented by a computer program. This computer program comprises machine instructions to implement the method when the computer program is run on or performed by a computer.

The detailed description is given for the example of mammary tomography, but it is easily within the reach of the person skilled in the art to adapt the description to any radiography by tomosynthesis, e.g. for standard radiology.

What is claimed is:

1. A method for positioning an object on a platform of an image acquisition system comprising a compression paddle and a detector underneath the platform, the method comprising:
   determining a positioning limit on the platform based on the distance separating the platform and the compression paddle, wherein the positioning limit on the platform is a limit beyond which the object must not lie.

2. The method of claim 1, wherein determining the positioning limit further comprises basing the positioning limit on the position of a light source relative to the detector.

3. The method of claim 1, wherein the image acquisition system acquires radiographic images by tomosynthesis, during which a radiation source is moved over different successive positions with respect to the detector.

4. The method of claim 3, wherein at least one image is acquired at each positon of the radiation source.

5. The method of claim 3, wherein the radiation source is moved from a starting position to a finishing position.

6. The method of claim 2, further comprising illuminating the platform with the light source to assist the positioning of the object on the platform.

7. The method of claim 2, wherein determining a positioning limit is performed by a drive unit of the image acquisition system.

8. The method of claim 7, wherein the drive unit controls the light source to mark the positioning limit by illuminating the platform.

9. The method of claim 8, wherein the light source illuminates part of the detector through the platform, the corresponding part of the platform defining an area in which the object is illuminated.

10. The method of claim 9, wherein the object is illuminated at all positions of the radiation source during acquisition of the images.

11. The method of claim 9, wherein the light source is positioned at a starting position of the radiation source during illumination of the detector and at a finishing position of the radiation source during illumination of the detector to mark the positioning limit.

12. The method of claim 11, wherein the starting position and the finishing position are symmetrical relative to a plane comprising, the center of a circular trajectory and the sectional plane.

13. The method of claim 11, wherein the radiation source defines a circular trajectory of a radius around a center when it is moved from one position to another position.

14. The method of claim 13, wherein the light source is positioned at a position perpendicular to the detector.

15. The method of claim 8, wherein the drive unit controls a collimator positioned under the light source, the collimator comprising plates actuated by the drive unit to delimit a portion of space to be illuminated based on the determined positioning limit.

16. An imaging system comprising:
   an acquisition unit comprising
   a detector;
   a platform underneath which the detector is placed for acquisition of images;
   a compression paddle; and
   a drive unit configured to determine a positioning limit on the platform, based on the distance separating the platform and the compression paddle, wherein the positioning limit on platform is a limit beyond which an object must not lie.

17. The imaging system of claim 16, further comprising a light source.

18. The imaging system of claim 17, wherein the drive unit determines a positioning limit on the platform based also on the position of the light source with respect to the detector.

19. The method of claim 18, further comprising a positioner configured to position the light source at acquisition positions with respect to the detector, wherein the detector is illuminated with the light source to mark out the positioning limit.

20. The method of claim 16, wherein the acquisition unit is configured to acquire radiographic images by tomosynthesis.

* * * * *